United States Patent [19]

Schurter et al.

[11] 4,067,725

[45] Jan. 10, 1978

[54] 3-PYRIDYL-OXY-ALKANECARBOXYLIC ACID AMIDES

[75] Inventors: Rolf Schurter, Binningen, Switzerland; Niels Clauson-Kaas, Farum, Denmark; Hermann Rempfler, Binningen, Switzerland

[73] Assignee: Ciba-Geigy Corporation, Ardsley, N.Y.

[21] Appl. No.: 715,351

[22] Filed: Aug. 18, 1976

[30] Foreign Application Priority Data

Aug. 25, 1975 Switzerland ............... 10963/75

[51] Int. Cl.$^2$ ............... A01N 9/22; C07D 213/56
[52] U.S. Cl. ............... 71/94; 260/268 H; 260/293.69; 260/294.8 D; 260/294.8 G; 260/294.9; 260/295.5 R; 260/295.5 A; 544/131
[58] Field of Search ............... 260/294.8 G, 295.5 A, 260/295.5 R, 295 AM; 71/94

[56] References Cited

U.S. PATENT DOCUMENTS

| | | | |
|---|---|---|---|
| 3,249,619 | 5/1966 | Johnston | 260/295 CA |
| 3,755,339 | 8/1973 | McKendry | 260/295 R |
| 3,761,486 | 9/1973 | McKendry | 260/295 AM |
| 3,987,050 | 10/1976 | Gulbenk | 260/294.8 F |
| 4,003,734 | 1/1977 | Johnston | 71/94 |
| 4,026,937 | 5/1977 | Gulbenk | 71/94 |

*Primary Examiner*—Alan L. Rotman

*Attorney, Agent, or Firm*—Harry Falber

[57] ABSTRACT

The present invention relates to 3-pyridyl-oxy-alkancarboxylic acid amides of formula

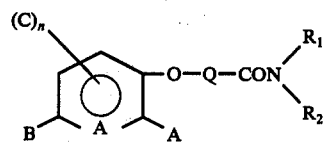

wherein
A and B are individually hydrogen, halogen, alkyl, cyano, nitro or amino,
C is hydrogen, halogen or nitro
$n$ is 1 or 2
Q is an aliphatic bridge, that can also be branched, unsaturated or substituted,
$R_1$ and $R_2$ independently are hydrogen, alkyl, alkoxy, alkenyl, alkynyl, phenyl or benzyl,
$R_1$ and $R_2$ together with the nitrogen atom to which they are bound are a 5 to 6 membered heterocycle.

The invention also relates to processes for the production of these amides, to their use as regulators of plant growth and as antidotes for herbicides, as well as to compositions containing these amides as active substance.

19 Claims, No Drawings

3-PYRIDYL-OXY-ALKANECARBOXYLIC ACID AMIDES

The present invention relates to 3-pyridyl-oxyalkanecarboxylic acid amides, to processes for producing them, to the use of these compounds as regulators of plant growth and as antidotes for herbicides, also to compositions containing such compounds as active substance.

The 3-pyridyl-oxy-alkanecarboxylic acid amides correspond to formula I

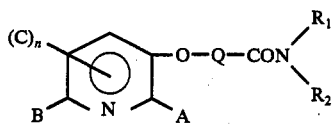

wherein

A is a hydrogen or halogen atom, a $C_1$-$C_4$-alkyl group which can be substituted by halogen or hydroxy, the cyano, nitro or amino group, a $C_1$-$C_4$-alkoxy or $C_1$-$C_4$-alkylthio group, a carbamoyl or $C_1$-$C_4$-alkoxy-carbonyl group, B has the same meaning as A, C is hydrogen, a halogen atom or the nitro group, n is 1 or 2, Q is an alkylene bridge member having 1-12 C atoms or an alkenylene bridge member having 2-12 C atoms which is branched or unbranched and which can be substituted by halogen or phenyl or by the

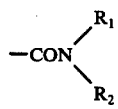

group, $R_1$ and $R_2$ independently of one another are each hydrogen, a $C_1$-$C_{12}$-alkyl group which is optionally substituted by OH or by $C_1$-$C_4$-alkoxy, a $C_1$-$C_4$-alkoxy group, a $C_3$-$C_8$-alkenyl group, a $C_3$-$C_8$-alkynyl group, phenyl or benzyl, whereby the phenyl rings can also be substituted by halogen, $C_1$-$C_4$-alkoxy, $C_1$-$C_4$-alkylthio, $C_1$-$C_4$-alkyl, $NO_2$ or cyano, $R_1$ and $R_2$ together with the nitrogen atom to which they are bound are also a 5-6-membered heterocycle, which can also embrace a further hetero atom, O, S or the —NH— or —$NR_3$ group, wherein $R_3$ is $C_1$-$C_4$-alkyl, phenyl or benzyl, or which can be substituted by $C_1$-$C_4$-alkyl.

Alkyl radicals in this formula are, also where they are a moiety of alkoxy or alkylthio groups, both branched-chain and straight-chain alkyl radicals having the given number of carbon atoms. The alkyl radicals $R_1$ and $R_2$ can be substituted by the hydroxyl group or can be interrupted by an oxygen atom; preferably also $R_1$ and $R_2$ are lower $C_1$-$C_4$-alkyl radicals. The alkenyl and alkynyl radicals $R_1$ and $R_2$ can have 3-8 carbon atoms; they are however preferably allyl, methallyl and propargyl radicals. The heterocyclic rings which $R_1$ and $R_2$ together with the nitrogen atom can form have 5 to 6 ring members and optionally a further hetero atom and are preferably saturated; the following may be mentioned as examples: the pyrrolidine, piperidine, methylpiperidine, morpholino, thiomorpholino, piperazine, methyl and phenylpiperazine rings.

The alkylene bridge member Q can contain up to 12 C atoms; it is preferably methylene or 1- or 2-alkylene or the 2-propylene bridge. The alkenylene bridge member is preferably a vinylene, allylene or methallylene group. These groups can be substituted by halogen atoms, by a phenyl group or by the

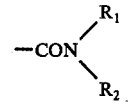

group.

The 3-pyridinol compounds of formula I are produced by reaction of a 3-pyridinol of formula II

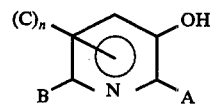

wherein A, B, C and n have the given meanings, with a halogenocarboxylic acid amide of formula III

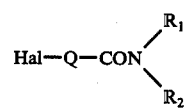

wherein Hal is a halogen atom, preferably chlorine or bromine, and Q, $R_1$ and $R_2$ have the given meanings, in the presence of a basic condensation agent and optionally in a polar solvent.

The said compounds can also be produced by the addition of a 3-pyridinol of formula II to a compound of formula IV

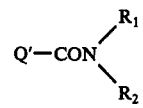

wherein $R_1$ and $R_2$ have the given meanings, and Q' is a twofold or threefold unsaturated radical having 2 to 12 C atoms, with substitution corresponding to Q.

The compound of formula IV is preferably a substituted amide of an alkenylcarboxylic acid, such as of acrylic acid, methacrylic acid, crotonic acid, 2-methylcrotonic acid, 3-methylcrotonic acid or 2- or 3-pentenyl acid, etc., or of an alkynylcarboxylic acid.

Finally, 3-pyridyl-oxy-alkanecarboxylic acids can be converted by known methods into amides either directly or by way of the corresponding acid halide.

Where they are not known, starting materials of formula II can be produced by the following methods and according to the given references.

3-Hydroxy-6-methylpyridine is produced from furfurylamine and formaldehyde by reaction with HCl/$H_2O$: see in this respect N. Clauson - Kaas et al., Acta. Chem. Scand. 21 (1967) 1104. For the production of 3-hydroxypyridine see, e.g., the British Patent Specification No. 862,581 or the German Patent Specification available for inspection No. 1,134,376. These can be subsequently converted by halogenation into other starting materials. 5-Chloro-3-hydroxypyridine can be produced from furfurylamine by reaction with chlorine/water. A further method is described in Czuba, Rocz. Chem. 34 (1960) 905-15. 3-Hydroxypyridine derivatives containing in the 2-position a cyano or amide function can be obtained according to the British Patent Specification No. 1,038,342 or according to N. Clauson - Kaas et al., Acta. Chem. Scand. 23 (1969), 1785. The introduction of a $CF_3$ group is effected by reaction of a carboxyl group with $SF_4$. 2,6-Dichloro-3-hydroxypyridine can be produced from 3-hydroxypyridine by nitration in the 2-position, subsequent reaction with hydrochloric acid and chlorination in the 6-position.

Suitable starting materials of formula III are the amides of halogenated alkanecarboxylic acids having 2-12 carbon atoms; thus, e.g., chloric and bromic acid amides, the amides of 2- and 3-chloro- and bromopropionic acid, and the alkanecarboxylic acids further substituted according to the meaning of Q, etc. Also suitable for this reaction, provided they are obtainable, are corresponding fluoro- or iodocarboxylic acid amides.

The 3-pyridinol compounds of the present invention have a regulating action on plant growth; in particular they inhibit the growth of dicotyledonous plants. Examples of the profitable application of the 3-pyridinol compounds according to the invention are, for example, the reduction of the vegetative growth of soya-bean plants and of similar leguminosae, which results in an increase in the yield of these crops; the inhibition of the undesirable growth of side shoots in the case of tobacco plants, the leading shoots of which have been cut, which inhibition promotes the formation of larger and better leaves; and the inhibition of the growth of large dicotyledonous plants, such as fruit trees, ornamental trees, bushes and hedges, with the object of reducing the extent of cutting operations.

Principally, however, these pyridine-3-oxy-alkanecarboxylic acid amides are used as antidotes together with herbicides which damage certain cultivated plants, in order to render possible the use of the respective herbicide as a selective herbicide in crops of these cultivated plants, where its action against weeds is required. The invention relates also to compositions which contain these amides, optionally together with a herbicide.

Certain herbicides from the most varied classes of substances, such as triazines, urea derivatives, carbamates, thiolcarbamates, halogenoacetanilides, halogenophenoxyacetic acids, etc., have an action against cultivated plants that is insufficient or not selective enough; these herbicides destroy, in addition to the weeds to be combatted, also the cultivated plants to a lesser or greater extent. The 3-pyridyl-oxy-alkanecarboxylic acid amides of the present invention have the capacity to specifically antagonise the harmful action of the herbicide on the cultivated plant, i.e. to protect the cultivated plant without appreciably affecting the herbicidal action on the weeds to be controlled. Depending on its properties, the antidote can be used before emergence (pre-emergence) or after emergence (post-emergence) of the plants: it can be used for pretreatment of the seed of the cultivated plant (seed dressing); or can be applied into the seed furrows; or it can be used for the pretreatment of cuttings; or finally it can be applied as a tank mixture; whereby it can be applied alone, or together with the herbicide. The treatment with the antidote can be carried out before or after the herbicidal treatment, or simultaneously. The pre-emergence treatment includes both the treatment of the cultivated area before sowing (ppi = pre plant incorporation) and the treatment of the sown cultivated area before emergence of the plants.

It has been shown that the 3-pyridyl-oxy-alkanecarboxylic acid amides suggested as antidotes specifically antagonise the herbicidal action of certain herbicides of the class including triazines, carbamates, halogenoacetanilides, etc. on gramineous crops, cereals such as wheat, rye, sorghum or rice, and in some cases also on dicotyledonous crops, such as soya bean, cotton or sugar cane, without impairing the herbicidal action on the weeds. In certain cases this action is even intensified.

The applied amount of the antidote varies between about 0.01 and about 10 parts by weight per part by weight of herbicide. The most suitable ratio with respect to the optimum action on a specific crop is determined from case to case, i.e. depending on the herbicide employed.

The antagonistic action of the antidote according to the invention does not however extend to the main weeds which are usually associated with the crops, e.g. weeds such as Echinochloa, Setaria italica, Digitaria sanguinalis, etc. These weeds are destroyed by the employed herbicides to practically the same high degree as they would be without the presence of the antidote.

Also insecticides, fungicides, etc., such as "Diazinon", "Captan", "Methoxychlor" and others, do not lose their effectiveness as a result of the presence of the antidote; such agents therefore can be concomitantly used where seed dressing is carried out.

Similarly good "safening" effects as in the case of triazines can be obtained on certain crops also with the use of other herbicides together with the 3-pyridyl-oxyalkanecarboxylic acid amides according to the invention.

The compounds of the present invention are negligibly toxic to warm-blooded animals, and the application of these compounds presents no problems. The amount applied is between 0.1 and 5 kg per hectare.

The said compounds have to our knowledge never been used in the field of agricultural chemistry. Similar pyridine compounds have become known, e.g., as biocidal, microbiocidal and fungicidal agents, or as agents for combatting animal pests, enteroparasites, see the U.S. Pat. No. 3,249,619 or the German 'Offenlegungsschrift' No. 2,103,728.

The compounds of the present invention are for the main part new compounds. Certain of them are described in Acta Chem. Scand. 23 (1969), pp. 1791-1796. Novel 3-pyridyl-oxyalkanecarboxylic acid amides of formula I are those wherein the bridge member Q is branched, or if unbranched is different from methylene.

Likewise novel are those 3-pyridyl-oxy-alkanecarboxylic acid amides of formula I wherein A, B, C, $n$, $R_1$ and $R_2$ have the given meanings and Q denotes the methylene bridge member (3-pyridyl-oxy-acetic acid amides), with the stipulation that if A is hydrogen, amino, the carbamoyl group or a $C_1$-$C_4$-alkoxycarbonyl group, B cannot be hydrogen, and if B is alkyl, A and C cannot simultaneously be hydrogen.

Compounds which have proved to be particularly excellent for inhibiting the growth of dicotyledonous plants and as antidotes for herbicides in gramineous crops are those compounds of formula I wherein A and B are each a halogen atom and C is hydrogen.

The production of the 3-pyridinol compounds according to the invention is to be further illustrated in the following Examples. Temperature values therein are expressed in degrees Centigrade.

EXAMPLE 1

N,N-diethyl-(2,6-dichloro-3-pyridyl)-oxy-acetic acid amide

A solution of 4.6 g of sodium methylate (0.2 mole) in 50 ml of absolute methanol is slowly added at room temperature to 33.4 g (0.2 mole) of 2,6-dichloropyridin-3-ol. There is then added, with gentle heating, 100 to 150 ml of dimethylsulphoxide until the cloudy solution becomes clear. The solution is then heated to 80°-90° and methanol is distilled off. The reaction solution is cooled and an addition is slowly made dropwise at 0°-10° C of a solution of 60 g (0.2 mole) of chloroacetic acid diethylamide (dissolved in 300 ml of dimethylsulphoxide). After the dropwise addition is completed, the reaction mixture is stirred at room temperature for a further hour. The solvent is distilled off under reduced pressure; the oil remaining is taken up in ether, washed with water, dried and freed from solvent to leave N,N-diethyl-(2,6-dichloro-3-pyridyl)-oxy-acetic acid amide, which boils at 137°/0.4 torr; yield: 35 g (62% of theory). Treatment with ethereal hydrochloric acid yields the hydrochloride, which is recrystallised from isopropanol.

EXAMPLE 2

N-Methyl-[2-(2,6-dichloro-3-pyridyl)-oxy]-propionic acid amide 17 ml of 40% aqueous methylamine (0.2 mole) is slowly added dropwise at 0°-5° C, with stirring and cooling in an ice bath, to a solution of 25 g (0.1 mole) of crude 2-[(2,6-dichloro-3-pyridyl)-oxy]-propionic acid chloride in 250 ml of benzene. After the dropwise addition is completed, stirring is maintained for one hour at room temperature. The organic solution is subsequently washed with water and dried; the solvent is removed in a rotary evaporator to leave, as a light-yellow oil which boils at 115°-123° C/0.01 torr, N-methyl-[2-(2,6-dichloro-3-pyridyl)-oxy]-propionic acid amide.

The acid chloride used as starting product is produced as follows:

a. 2,6-dichloro-3-pyridinol 100 g (0.77 mole) of 2-chloro-3-pyridinol is dissolved in 350 ml of dimethylformamide. In the course of 1.5 hours, 70 ml of chlorine (measured at −80°; 0.93 mole) is introduced at 0° into the stirred solution. The reaction mixture is subsequently stirred for 1.5 hours at 20° C and afterwards concentrated in a rotary evaporator (bath: 50°; 10 torr). To the residue are added 400 ml of water and 100 ml of ether. The two phases are separated, and the aqueous phase is extracted 5 times with 100 ml of ether each time. The combined ether phases are washed with water and dried. The solvent is removed in vacuo; the semisolid residue is stirred with 1.6 liters of water, and the resulting suspension is adjusted to pH 3. The suspension is heated to boiling, and after a few minutes the solution is decanted from an oily residue. The solution is purified with active charcoal, and the yellow product, obtained on cooling, is recrystallised from water; m.p. 136°-138° C; yield: 42 g;

b. 2-[(2,6-dichloro-3-pyridyl)oxy]propionic acid ethyl ester 164 g (1 mole) of 2,6-dichloro-3-pyridinol, 1500 ml of acetonitrile, 253.4 g (1.4 moles) of 2-bromopropionic acid ethyl ester and 127.2 (1.2 moles) of sodium carbonate are refluxed for 3 hours. The reaction mixture is then cooled, filtered, and concentrated in a rotary evaporator. The residue is taken up in ether and washed with 2N sodium hydroxide solution. After drying with magnesium sulphate, the solution is concentrated by evaporation and distilled in vacuo; a clear oil distills at 110°-140°/0.1 torr; yield: 200 g; i $n_D^{25}$: 1.5200. Crystallisation from benzene/petroleum ether yields a product having a melting point of 41°-46°;

c. 2-[(2,6-dichloro-3-pyridyl)oxy]propionic acid 105 g of 2-[(2,6-dichloro-3-pyridyl)oxy]propionic acid ethyl ester is refluxed with 550 ml of 1N sodium hydroxide solution for 1 hour. The pH value of the solution is brought to 1.5 with concentrated hydrochloric acid and the solution is filtered. Recrystallisation in ethanol/water yields 58 g of the above acid; m.p. 128°-131°;

d. 2[(2,6-dichloro-3-pyridyl)oxy]propionic acid chloride 23.6 g (0.1 mole) of 2-[(2,6-dichloro-3-pyridyl)oxy]propionic acid, 150 ml of chloroform and 1.5 ml of dimethylformamide are heated with stirring to 55°, and in the course of 1 hour a solution of 18 g (0.15 mole) of thionyl chloride in 40 ml of chloroform is added dropwise. The reaction mixture is subsequently refluxed for 16 hours and is afterwards concentrated in vacuo. The product obtained is used directly for further reactions.

| No. | A | B | C | Q | $R_1$ | $R_2$ | Physical characteristics |
|---|---|---|---|---|---|---|---|
| 1 | $NH_2$ | $CH_3$ | H | $-CH_2-$ | $C_2H_5$ | $C_2H_5$ | m.p. 95 – 97° |
| 2 | Cl | Cl | H | $-CH-$<br>$\|$<br>$CH_3$ | H | $CH_3$ | m.p. 168° |
| 3 | Cl | Cl | H | $-CH-$<br>$\|$<br>$CH_3$ | H | $-CH-C\equiv CH$ | |
| 4 | Cl | Cl | H | $-CH-$<br>$\|$<br>$CH_3$ | H | $isoC_3H_7$ | m.p. 135° |
| 5 | Cl | Cl | H | $-CH-$<br>$\|$<br>$CH_3$ | H | $CH(C_2H_5)_2$ | |

-continued $$\underset{B}{\overset{C}{\underset{}{\bigg|}}}\text{piperidine with }O-Q-CONR_1R_2$$

| No. | A | B | C | Q | $R_1$ | $R_2$ | Physical characteristics |
|---|---|---|---|---|---|---|---|
| 6 | Cl | Cl | H | $-CH(CH_3)-$ | H | $nC_8H_{17}$ | m.p. 94 – 95° |
| 7 | Cl | Cl | H | $-CH(CH_3)-$ | H | $CH_2-CH=CH_2$ | m.p. 97 – 99° |
| 8 | Cl | Cl | H | $-CH(CH_3)-$ | H | $C_2H_4OH$ | |
| 9 | Cl | Cl | H | $-CH(CH_3)-$ | H | $C_2H_4OCH_3$ | |
| 10 | Cl | Cl | H | $-CH(CH_3)-$ | H | $CH_2$-phenyl | |
| 11 | Cl | Cl | H | $-CH(CH_3)-$ | H | phenyl | m.p. 109 – 110° |
| 12 | Cl | Cl | H | $-CH(CH_3)-$ | $CH_3$ | $CH_3$ | m.p. 93 – 96° |
| 13 | Cl | Cl | H | $-CH(CH_3)-$ | $CH_3$ | $OCH_3$ | m.p. 59 – 60° |
| 14 | Cl | Cl | H | $-CH(CH_3)-$ | \multicolumn{2}{c}{cyclopentyl ($R_1R_2N$=)} | m.p. 108 – 109° |
| 15 | Cl | Cl | H | $-CH(CH_3)-$ | \multicolumn{2}{c}{cyclohexyl ($R_1R_2N$=)} | m.p. 114 – 116° |
| 16 | Cl | Cl | H | $-CH(CH_3)-$ | \multicolumn{2}{c}{4-methylcyclohexyl ($R_1R_2N$=)} | m.p. 74 – 78° |
| 17 | Cl | Cl | H | $-CH(CH_3)-$ | \multicolumn{2}{c}{2-methylcyclohexyl ($R_1R_2N$=)} | |
| 18 | Cl | Cl | H | $-CH(CH_3)-$ | \multicolumn{2}{c}{4-methylpiperazinyl} | |
| 19 | Cl | Cl | H | $-CH(CH_3)-$ | \multicolumn{2}{c}{morpholinyl} | m.p. 108 – 109° |
| 20 | Cl | Cl | H | $-CH(CH_3)-$ | \multicolumn{2}{c}{tetrahydro-1,3-oxazinyl} | |
| 21 | Cl | Cl | H | $-CH(CH_3)-$ | \multicolumn{2}{c}{thiazolidinyl} | |
| 22 | Cl | Cl | H | $-CH(CH_3)-$ | \multicolumn{2}{c}{pyrrolyl} | |

-continued

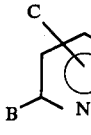

| No. | A | B | C | Q | $R_1$ | $R_2$ | Physical characteristics |
|---|---|---|---|---|---|---|---|
| 23 | Cl | Cl | H | −CH(CH$_3$)− | H | H | m.p. 118 – 120° |
| 24 | Cl | Cl | H | −CH(CH$_3$)− | CH$_2$−CH=CH$_2$ | CH$_2$−CH=CH$_2$ | $n_D^{35}$ 1.5448 |
| 25 | Cl | Cl | H | −CH(CH$_3$)− | C$_2$H$_5$ | C$_2$H$_5$ | $n_D^{20}$ 1.5405 |
| 26 | Cl | Br | H | −CH(CH$_3$)− | nC$_8$H$_{17}$ | H | m.p. 98 – 102° |
| 27 | Cl | Br | H | −CH(CH$_3$)− | CH$_2$−CH=CH$_2$ | H | m.p. 111 – 113° |
| 28 | Cl | Br | H | −CH(CH$_3$)− | H | H | m.p. 141 – 144° |
| 29 | Cl | Br | H | −CH(CH$_3$)− | C$_6$H$_5$ (phenyl) | H | m.p. 107 – 112° |
| 30 | Cl | Br | H | −CH(CH$_3$)− | 2-methyl-3-methyl-chlorophenyl | | m.p. 170 – 174° |
| 31 | Cl | Br | H | −CH(CH$_3$)− | CH$_2$−CH=CH$_2$ | CH$_2$−CH=CH$_2$ | $n_D^{35}$ 1.5560 |
| 32 | Cl | Br | H | −CH(CH$_3$)− | C$_2$H$_5$ | C$_2$H$_5$ | $n_D^{20}$ 1.5555 |
| 33 | Cl | Cl | H | −CH(nC$_8$H$_{17}$)− | CH$_3$ | CH$_3$ | $n_D^{25}$ 1.5195 |
| 34 | Cl | Br | H | −CH(CH$_3$)− | CH$_3$ | CH$_3$ | m.p. 103° |
| 35 | Cl | Br | H | −C$_3$H$_6$− | CH$_3$ | CH$_3$ | m.p. 114° |
| 36 | Cl | Br | H | −CH(C$_2$H$_5$)− | CH$_3$ | CH$_3$ | $n_D^{25}$ 1.5545 |
| 37 | Cl | Br | H | −CH(nC$_8$H$_{17}$)− | CH$_3$ | CH$_3$ | $n_D^{25}$ 1.5305 |
| 38 | Br | Br | H | −CH(CH$_3$)− | CH$_3$ | CH$_3$ | m.p. 98 – 100° |
| 39 | Cl | Cl | H | −CH(CH$_3$)− | C$_2$H$_5$ | C$_2$H$_5$ |  |
| 40 | Cl | Cl | H | −CH(C$_2$H$_5$)− | CH$_3$ | CH$_3$ | $n_D^{25}$ 1.5465 |
| 41 | Cl | Cl | H | −C$_3$H$_6$− | CH$_3$ | CH$_3$ | m.p. 96° |
| 42 | Cl | Cl | H | −C$_{10}$H$_{20}$− | CH$_3$ | CH$_3$ |  |
| 43 | Cl | Cl | H | −CH(cyclohexyl)− | CH$_3$ | CH$_3$ |  |
| 44 | Cl | Cl | H | −C(CH$_3$)=CH− | CH$_3$ | CH$_3$ |  |
| 45 | CN | H | H | −CH(CH$_3$)− | CH$_3$ | CH$_3$ |  |

-continued $$\begin{array}{c} C \\ | \\ B-\underset{N}{\underset{|}{\bigcirc}}-A \end{array} \quad O-Q-CONR_1R_2$$

| No. | A | B | C | Q | $R_1$ | $R_2$ | Physical characteristics |
|---|---|---|---|---|---|---|---|
| 46 | $CF_3$ | H | H | $-CH(CH_3)-$ | $CH_3$ | $CH_3$ | |
| 47 | Cl | Br | H | $-CH(CH_3)-$ | (cyclopentyl) | | m.p. 115 – 121° |
| 48 | Cl | Br | H | $-CH(CH_3)-$ | (cyclohexyl) | | m.p. 115 – 120° |
| 49 | Cl | Br | H | $-CH(CH_3)-$ | (tetrahydropyranyl-O) | | m.p. 102 – 104° |
| 50 | Cl | H | H | $-CH(CH_3)-$ | $CH_3$ | $CH_3$ | m.p. 95 – 97° |
| 51 | $CONH_2$ | H | H | $-CH(CH_3)-$ | $CH_3$ | $CH_3$ | m.p. 154 – 156° |
| 52 | $COOCH_3$ | H | H | $-CH(CH_3)-$ | $CH_3$ | $CH_3$ | m.p. 76 – 78° |
| 53 | $CH_2OH$ | $CH_3$ | H | $-CH(CH_3)-$ | $CH_3$ | $CH_3$ | m.p. 87 – 90° |
| 54 | $NO_2$ | $CH_3$ | H | $-CH(CH_3)-$ | $CH_3$ | $CH_3$ | m.p. 125 – 127° |
| 55 | $CH_3$ | $CH_3$ | H | $-CH(CH_3)-$ | $CH_3$ | $CH_3$ | m.p. 71 – 73° |
| 56 | H | H | Cl(5) | $-CH(CH_3)-$ | $CH_3$ | $CH_3$ | m.p. 45 – 53° |
| 57 | H | H | H | $-CH(CH_3)-$ | $CH_3$ | $CH_3$ | m.p. 92 – 96° |
| 58 | F | H | H | $-CH(CH_3)-$ | $CH_3$ | $CH_3$ | m.p. 93 – 94° |
| 59 | $NH_2$ | H | H | $-CH(CH_3)-$ | $CH_3$ | $CH_3$ | m.p. 136 – 137° |
| 60 | H | $CH_3$ | H | $-CH(CH_3)-$ | $CH_3$ | $CH_3$ | m.p. 71 – 73° |
| 61 | $NH_2$ | $CH_3$ | H | $-CH(CH_3)-$ | $CH_3$ | $CH_3$ | m.p. 130 – 131° |
| 62 | $COOCH_3$ | $CH_3$ | H | $-CH(CH_3)-$ | $CH_3$ | $CH_3$ | m.p. 80 – 85° |
| 63 | $NO_2$ | H | H | $-CH(CH_3)-$ | $CH_3$ | $CH_3$ | m.p. 110 – 112° |
| 64 | Br | H | H | $-CH(CH_3)-$ | $CH_3$ | $CH_3$ | m.p. 93 – 96° |
| 65 | $CH_2N(CH_3)_2$ | H | H | $-CH(CH_3)-$ | $CH_3$ | $CH_3$ | $n_D^{25}$ 1.5239 |
| 66 | $CH_3$ | $CH_3$ | H | $-CH(CH_3)-$ | $C_2H_5$ | $C_2H_5$ | m.p. 79 – 81° |
| 67 | Cl | Cl | H | $-CH_2-$ | $CH_3$ | $CH_3$ | m.p. 86 – 88° |
| 68 | $CH_3$ | $CH_3$ | H | $-CH_2-$ | $CH_3$ | $CH_3$ | |
| 69 | Cl | Br | H | $-CH_2-$ | $CH_3$ | $CH_3$ | m.p. 89 – 90° |

-continued $$\underset{B}{\overset{C}{\underset{N}{\bigcirc}}} \underset{A}{O-Q-CONR_1R_2}$$

| No. | A | B | C | Q | R$_1$ | R$_2$ | Physical characteristics |
|-----|---|---|---|---|-------|-------|--------------------------|
| 70 | NO$_2$ | CH$_3$ | Br(4) | —CH(CH$_3$)— | CH$_3$ | CH$_3$ | m.p. 118 – 120° |
| 71 | Cl | CH$_3$ | NO$_2$(4) | —CH(CH$_3$)— | CH$_3$ | CH$_3$ | m.p. 62 – 64° |
| 72 | Cl | CH$_3$ | Cl(4) | —CH(CH$_3$)— | CH$_3$ | CH$_3$ | n$_D^{20}$ 1.5423 |
| 73 | Cl | Br | Br(4) | —CH(CH$_3$)— | CH$_3$ | CH$_3$ | n$_D^{35}$ 1.5870 |
| 74 | Br | Br | Cl(5) | —CH(CH$_3$)— | CH$_3$ | CH$_3$ | m.p. 159 – 161° |
| 75 | Cl | CH$_3$ | NO$_2$(4) | —CH(CH$_3$)— | —(CH$_2$)$_4$— (pyrrolidinyl) | | |
| 76 | Cl | CH$_3$ | NO$_2$(4) | —CH(CH$_3$)— | CH$_2$—CH=CH$_2$ | H | |
| 77 | Cl | CH$_3$ | NO$_2$(4) | —CH(CH$_3$)— | C$_6$H$_5$ | H | |
| 78 | Cl | CH$_3$ | Cl(4) | —CH(CH$_3$)— | C$_2$H$_5$ | C$_2$H$_5$ | m.p. 96 – 98° |
| 79 | Cl | CH$_3$ | Cl(4) | —CH(CH$_3$)— | —(CH$_2$CH$_2$)$_2$O— (morpholinyl) | | m.p. 75 – 78° |
| 80 | Cl | CH$_3$ | Cl(4) | —CH(CH$_3$)— | CH$_2$—CH=CH$_2$ | CH$_2$—CH=CH$_2$ | m.p. 91 – 93° |
| 81 | Cl | CH$_3$ | Cl(4) | —CH(CH$_3$)— | CH$_2$—CH=CH$_2$ | H | m.p. 62 – 65° |
| 82 | Cl | CH$_3$ | Cl(4) | —CH$_2$— | CH$_3$ | CH$_3$ | |
| 83 | Cl | CH$_3$ | NO$_2$(4) | —CH$_2$— | CH$_3$ | CH$_3$ | |
| 84 | Cl | Cl | H | —C(CH$_3$)(CON(CH$_3$)$_2$)— | CH$_3$ | CH$_3$ | m.p. 141 – 142° |
| 85 | Cl | CH$_3$ | H | —CH$_2$— | C$_2$H$_5$ | C$_2$H$_5$ | |
| 86 | Br | Br | Br(4) | —CH(CH$_3$)— | CH$_3$ | CH$_3$ | m.p. 83 – 84° |
| 87 | H | H | H | —CH$_2$— | C$_2$H$_5$ | C$_2$H$_5$ | n$_D^{25}$ 1.5267 known |
| 88 | NH$_2$ | H | H | —CH$_2$— | H | H | known m.p. 154 – 156° |
| 89 | CH$_2$OH | H | H | —CH$_2$— | H | H | known m.p. 157 – 158° |
| 90 | COOCH$_3$ | H | H | —CH$_2$— | H | H | known m.p. 185 – 186° |
| 91 | CONH$_2$ | H | H | —CH$_2$— | C$_2$H$_5$ | C$_2$H$_5$ | known m.p. 134 – 135° |

The application of the 3-pyridyl-oxy-alkanecarboxylic acid amides of the present invention as antidotes for herbicides.

1. Application as tank mixture

A liquid preparation of a mixture of antidote and herbicide (quantitative proportion between 10 : 1 and 1 : 10) is used, whereby the applied amount of herbicide is 0.1 to 10 kg per hectare. This tank mixture is preferably applied before emergence (either before or after sowing), or it is worked into the unsown soil to a depth of 5–10 cm.

2. Seed dressing a. Dressing of the seeds with an antidote formulated as a wettable powder by shaking in a vessel until there is an even distribution over the surface of the seeds (dry dressing). The amount of antidote used for this purpose is about 10 to 500 g (40 g to 2 kg of wettable powder) per 100 kg of seed.

b. Dressing of the seeds with an emulsion concentrate of the antidote by the method and with the amounts as given under a) (wet dressing).

c. Dressing by immersion of the seeds in a liquor containing 50–3200 ppm of antidote for 1–20 hours and subsequent drying of the seeds (immersion dressing).

3. Application into the seed furrow

The antidote is introduced, as emulsion concentrate, wettable powder or granulate, into the open sown seed furrow and, after covering of the seed furrow in the normal manner, the herbicide is applied either before or after emergence of the plants.

The antidote can be applied before, together with, or after the herbicide, and its application to the seeds or to the field before emergence can be effected either before or after sowing; or in certain cases it can be effected also after germination of the seed (post-emergence).

If the antidote is applied simultaneously with the herbicide, this is accomplished by use of a preparation according to the invention, which preparation contains the 3-pyridyl-oxy-alkanecarboxylic acid amide and a herbicide together with additives.

Such preparations are either in the solid form, such as dusts, scattering agents and granulates, or in the liquid form, such as solutions and aqueous dispersions; or they are in the form of water-dispersible concentrates of active substance, such as wettable powders, emulsion concentrates or pastes.

In order to determine the selective herbicidal action, 2-methylthio-4-ethylamino-6-tert.-butylamino-s-triazine (IGRAN) was tested on its own and together with 3-pyridyloxy-alkanecarboxylic acid amides of formula I in cultivated crops of millet of the varieties "Funk", "Dekalb" and "Mastergold".

1. Post-emergence application as tank mixture

Aqueous stock liquors (suspensions) from formulated wettable powders of the herbicide "Igran" (denoted by H) and an antidote of formula I according to the invention were produced; and these were then applied, either individually or as mixtures at the given concentrations and in the given mixture ratios, to the emerged plants in the 2–3-leaf stage of various kinds of cultivated millet, namely Sorghum hybridum (varieties "Funk", "Dekalb" and "Mastergold"), sown in pots or in seed trays in the greenhouse, the said liquors being applied to the surface of the soil in the sown vessels. The pots or seed trays were then kept at 22°–23° C with the required watering, and the results were evaluated after 15–18 days according to the following scale of values:

9 = plants undamaged (as in the case of the untreated control plants),
1 = plants completely destroyed,
2 to 8 = intermediate stages of damage.

The results are summarised in the following Table I. The concentration values in kg/hectare in relation to the other units of measure are as follows:

1 kg/hectare = 0.1 g/m$^2$ = 2 mg per liter of soil (since seed trays and pots are filled with soil to a depth of 5 cm).

Table 1

| Applied amount in kg/hectare | | | Sorghum hybridum | | |
|---|---|---|---|---|---|
| Igran H | Mixture M | Compound No. 12 S | "Funk" H M S | "Dekalb" H M S | "Master-gold" H M S |
| 4 | 4 + 4 | 4 | 2 4 9 | 1 3 9 | 1 3 9 |
| 2 | 2 + 4 | 4 | 3 6 9 | 2 3 9 | 2 3 9 |
| 2 | 2 + 2 | 2 | 3 6 9 | 2 4 9 | 2 4 9 |
| 1 | 1 + 2 | 2 | 5 7 9 | 3 6 9 | 3 6 9 |
| 1 | 1 + 1 | 1 | 5 8 9 | 3 6 9 | 3 5 9 |

Table 1-continued

| Applied amount in kg/hectare | | | Sorghum hybridum | | |
|---|---|---|---|---|---|
| Igran H | Mixture M | Compound No. 12 S | "Funk" H M S | "Dekalb" H M S | "Master-gold" H M S |
| | | Compound No. 34 | | | |
| 2 | 2 + 2 | 2 | 1 4 9 | 1 2 9 | 1 3 9 |
| | | Compound No. 38 | | | |
| 2 | 2 + 2 | 2 | 1 4 9 | 1 2 9 | 1 3 9 |
| | | Compound No. 71 | | | |
| 4 | 4 + 4 | 4 | 1 3 9 | | 1 4 9 |
| 2 | 2 + 4 | 4 | 1 5 9 | | 159 |
| 2 | 2 + 2 | 2 | 1 4 9 | | 1 7 9 |
| 1 | 1 + 2 | 2 | 2 8 9 | | 3 7 9 |
| 1 | 1 + 1 | 1 | 2 7 9 | | 3 7 9 |
| | | Compound No. 72 | | | |
| 4 | 4 + 4 | 4 | 1 2 9 | | 1 2 9 |
| 2 | 2 + 4 | 4 | 1 3 9 | | 1 2 9 |
| 2 | 2 + 2 | 2 | 1 2 9 | | 1 5 9 |
| 1 | 1 + 2 | 2 | 229 | | 3 2 9 |
| 1 | 1 + 1 | 1 | 2 8 9 | | 3 6 9 |
| | | Compound No. 86 | | | |
| 2 | 2 + 2 | 2 | 1 3 9 | 2 5 9 | 1 3 9 |

It is seen that the cultivated millet varieties are less damaged with application of various mixture ratios at different concentrations, whereas with application of the herbicide alone they are destroyed even at low concentrations.

2. Seed dressing (wet)

Aqueous emulsion concentrates (liquid) of the antidote according to the invention are prepared, and the cultivated-millet seeds (50 g of seed) in a bottle are treated therewith by shaking. The various concentrations of antidote are expressed in grams of antidote per 100 kg of seed. Shortly after this dressing treatment, the seeds are sown in pots or in seed trays, and when the plants have emerged and have attained the 2–3-leaf stage they are treated in the usual manner with spray liquors of the herbicide as under 1) (post-emergence). The evaluation of the results is made 15 days after application of the herbicide using the same scale of values; the results are given in the following Table II:

Table II

| Applied amount | | Sorghum hybridum | | |
|---|---|---|---|---|
| Igran | Compound No. 12 | "Funk" H M S | "Dekalb" H M S | "Master-gold" H M S* |
| 4 kg/ha | 400g/100 kg seed | 2 4 9 | 1 2 9 | 1 3 9 |
| 4 | 200 | 2 5 9 | 1 4 9 | 1 4 8 |
| 4 | 100 | 2 4 9 | 1 3 9 | 1 5 9 |
| 4 | 50 | 2 4 9 | 1 2 9 | 1 4 9 |
| 2 | 400g/100kg of seed | 3 5 9 | 2 4 9 | 2 4 7 |
| 2 | 200 | 3 7 9 | 2 6 9 | 3 7 8 |
| 2 | 100 | 3 6 9 | 2 5 9 | 2 5 9 |
| 2 | 50 | 3 5 9 | 2 3 9 | 2 4 9 |
| 1 | 400 | 5 6 9 | 3 5 9 | 3 5 7 |
| 1 | 200 | 5 7 9 | 3 7 9 | 3 4 8 |
| 1 | 100 | 5 7 9 | 3 4 9 | 3 5 9 |
| 1 | 50 | 5 6 9 | 3 2 9 | 3 3 9 |
| | compound No. 34 | | | |
| 2 kg/ha | 200g/100kg of seed | 1 6 9 | | |
| 2 | 100 | 1 6 9 | | |
| 1 | 200 | 2 8 9 | | |
| 1 | 100 | 2 7 9 | | |
| Igran | Compound No. 38 | | | |
| 2 kg/ha | 200g/100kg of seed | 1 8 9 | 1 6 9 | 1 5 9 |
| 2 | 100 | 1 7 9 | 1 5 9 | 1 6 9 |
| 1 | 200 | 2 8 9 | 1 4 9 | 1 6 9 |
| 1 | 100 | 2 8 9 | 1 5 9 | 1 8 9 |
| | | Sorghum hybridum | | |
| Igran | Compound No. 71 | "Funk" H M S | "Dekalb" H M S | "Master-gold" H M S |
| 4 kg/ha | 400g/100kg of seed | 1 6 9 | | 1 8 9 |
| 4 | 200 | 1 5 9 | | 1 5 9 |

Table II-continued

| | | | |
|---|---|---|---|
| 4 | 100 | 1 4 9 | 1 4 9 |
| 4 | 50 | 1 2 9 | 1 2 9 |
| 2 | 400 | 1 8 9 | 1 7 9 |
| 2 | 200 | 1 8 9 | 1 8 9 |
| 2 | 100 | 1 5 9 | 1 6 9 |
| 2 | 50 | 1 2 9 | 1 3 9 |
| 1 | 400 | 2 8 9 | 3 9 9 |
| 1 | 200 | 2 9 9 | 3 9 9 |
| 1 | 100 | 2 8 9 | 3 8 9 |
| 1 | 50 | 2 7 9 | 3 7 9 |
| Igran | Compound No. 72 | | |
| 4 kg/ha | 400g/100kg of seed | 1 8 8 | 1 8 8 |
| 4 | 200 | 1 7 9 | 1 8 8 |
| 4 | 100 | 1 8 9 | 1 8 9 |
| 4 | 50 | 1 6 9 | 1 7 9 |
| 2 | 400 | 1 8 8 | 1 8 8 |
| 2 | 200 | 1 9 9 | 1 8 8 |
| 2 | 100 | 1 9 9 | 1 9 9 |
| 2 | 50 | 1 8 9 | 1 9 9 |
| 1 | 400 | 2 8 8 | 3 7 8 |
| 1 | 200 | 2 9 9 | 3 9 8 |
| 1 | 100 | 2 9 9 | 3 9 9 |
| 1 | 50 | 2 9 9 | 3 9 9 |

H: = herbicide tested with undressed seed
M: = herbicide tested with dressed seed
S: = dressed seed tested without herbicide 3. Post-emergence application "into the seed furrow"

The pots or seed trays are treated with active-substance liquors of 3-pyridyl-oxy-alkanecarboxylic acid amides and immediately afterwards are sown with seeds of the cultivated millet. When the small plants have emerged and have reached the 3-leaf-stage — which takes about 2 weeks — the herbicide is sprayed on. The pots or seed trays are then further treated in a greenhouse as already described. An evaluation is made 15 days after application of the herbicide, using the same scale of values as before; the results are summarised in Table III:

Table III

| Applied amount in kg/hectare | | | Sorghum hybridum | | |
|---|---|---|---|---|---|
| Igran H | Mixture M | Compound No. 12 S | "Funk" H M S | "Dekalb" H M S | "Master-gold" H M S |
| 4 | 4 + 4 | 4 | 2 6 9 | 1 4 8 | 1 3 9 |
| 4 | 4 + 2 | 2 | 2 6 9 | 1 4 9 | 1 3 9 |
| 4 | 4 + 1 | 1 | 2 6 9 | 1 2 9 | 1 2 9 |
| 2 | 2 + 4 | 4 | 3 8 9 | 2 5 9 | 2 6 9 |
| 2 | 2 + 2 | 2 | 3 8 9 | 2 3 9 | 2 6 9 |
| 2 | 2 + 1 | 1 | 3 7 9 | 2 4 9 | 2 5 9 |
| 1 | 1 + 4 | 4 | 5 8 9 | 3 6 8 | 3 6 9 |
| 1 | 1 + 2 | 2 | 5 8 9 | 3 4 9 | 3 6 9 |
| 1 | 1 + 1 | 1 | 5 8 9 | 3 5 9 | 3 7 9 |
| | | Compound No. 38 | | | |
| 2 | 2 + 2 | 2 | 1 7 9 | 1 6 9 | 1 6 9 |
| 1 | 1 + 1 | 1 | 2 8 9 | 1 7 9 | 3 3 9 |

| Applied amount in kg/hectare | | | Sorghum hybridum | | |
|---|---|---|---|---|---|
| Igran H | Mixture M | Compound No. 72 S | "Funk" H M S | "Dekalb" H M S | "Master-gold" H M S |
| 4 | 4 + 4 | 4 | 1 4 9 | | 1 5 9 |
| 4 | 4 + 2 | 2 | 1 4 9 | | 1 5 9 |
| 4 | 4 + 1 | 1 | 1 3 9 | | 1 3 9 |
| 2 | 2 + 4 | 4 | 1 6 9 | | 1 4 9 |
| 2 | 2 + 2 | 2 | 1 6 9 | | 1 4 9 |
| 1 | 1 + 4 | 4 | 2 7 9 | | 1 5 9 |
| 1 | 1 + 2 | 2 | 2 8 9 | | 3 7 9 |
| 1 | 1 + 1 | 1 | 2 8 9 | | 3 6 9 |
| 1 | 1 + 1 | 1 | 2 8 9 | | 3 4 9 |

These results show that in cases where the concentrations of herbicide are low, but sufficiently high to control weeds, it is possible to apply the 3-pyridyl-oxy-carboxylic acid amide used as antidote in such a manner that the employed variety of cultivated millet remains to a great extent unharmed.

The compositions according to the invention are produced in a manner known per se by the intimate mixing and/or grinding of active substances of the general formula I with suitable carriers, optionally with the addition of dispersing agents or solvents which are inert to the active substances. The active substances can be used as dusts, scattering agents, granulates (coated granulates, impregnated granulates and homogeneous granulates), wettable powders, pastes, emulsions, solutions or aerosols.

The solid preparations (dusts, scattering agents and granulates) are produced by the mixing of the active substances with solid carriers. The particle size of the carriers is for dusts advantageously up to about 0.1 mm; for scattering agents about 0.075 to 0.2 mm; and for granulates 0.2 mm or coarser.

The concentration of active substance in the solid preparations is as a rule 0.5 to 80%. It is possible to add to these mixtures also additives stabilising the active substance, and/or nonionic, anion-active and cation-active substances which improve, e.g., the adhesiveness of the active substances on plants and parts of plants (adhesives and agglutinants), and/or ensure better wettability (wetting agents) as well as dispersibility (dispersing agents).

Water-dispersible concentrates of active substances, i.e. wettable powders, pastes and emulsion concentrates, are agents which can be diluted with water to obtain any desired concentration. They consist of active substance, carrier, optionally additives stabilising the active substance, surface-active substances and anti-foaming agents and, optionally, solvents. The concentration of active substance in these preparations is 5 - 80%. The wettable powders and pastes are obtained by the mixing and grinding of the active substances with dispersing agents and pulverulent carriers, in suitable devices, until homogeneity is obtained. In some cases it is advantageous to use mixtures of various carriers. Suitable anti-foaming agents are, e.g., silicones. The active substances are so mixed, ground, sieved and strained with the aforementioned additives that the solid constituent in the case of wettable powders has a particle size not exceeding 0.02 to 0.04 mm, and in the case of pastes not exceeding 0.003 mm. Dispersing agents, organic solvents and water are used to produce emulsion concentrates and pastes. The solvents must be practically odourless, nonphytotoxic, inert to the active substances and not readily combustible.

Furthermore, the agents according to the invention can be used in the form of solutions. For this purpose, the active substance, or several active substances, of the general formula I is (or are) dissolved in suitable organic solvents, solvent mixtures or water. The solutions should contain the active substances in a concentration of 1 to 20%.

Other biocidal active substances or agents can be mixed with the described compositions of the invention. For the broadening of their sphere of action, the new compositions can for example contain, in addition to the stated compounds of the general formula I and other herbicides: insecticides, fungicides, bactericides, fungistatics, bacteriostatics or nematocides. The compositions of the invention may also contain fertilisers, trace elements, etc.

Granulate

The following substances are used to produce a 5% granulate:

5 parts of N,N-diethyl-(2,6-dichloro-3-pyridyl-oxyacetic acid amide, 0.25 part of epichlorohydrin,
0.25 part of cetyl polyglycol ether with 8 moles of ethylene oxide,
3.50 parts of polyglycol ("Carbowax"),
91 parts of kaolin (particle size 0.3 - 0.8 mm).

The active substance is mixed with epichlorohydrin and the mixture is dissolved in 6 parts of acetone; the polyglycol and cetyl polyglycol ether are then added. The resulting solution is sprayed onto kaolin and the acetone is subsequently evaporated off in vacuo.

Wettable powders

The following constituents are used to produce
a) a 50%, b) a 25% and c) a 10% wettable powder:
a.
 50 parts of 2-[(2,6-dichloro-3-pyridyl)-oxy]-propionic acid amide,
 5 parts of sodium dibutyl-naphthalene sulphonate,
 3 parts of naphthalenesulphonic acid/phenolsulphonic acid/formaldehyde condensate 3:2:1,
 20 parts of kaolin,
 22 parts of Champagne chalk;
b.
 25 parts of the above Active Substance,
 5 parts of the sodium salt of oleyl methyl tauride,
 2.5 parts of naphthalenesulphonic acid/formaldehyde condensate,
 0.5 part of carboxymethylcellulose,
 5 parts of neutral potassium aluminium silicate,
 62 parts of kaolin;
c.
 10 parts of the above Active Substance,
 3 parts of a mixture of the sodium salts of saturated fatty alcohol sulphates,
 5 parts of naphthalenesulphonic acid/formaldehyde condensate,
 82 parts of kaolin.

The given active substance is absorbed onto the appropriate carriers (kaolin and chalk) and subsequently mixed and ground with the other constituents. Wettable powders having excellent wetting and suspension properties are obtained. It is possible to obtain from such wettable powders, by dilution with water, suspensions of the desired concentration. These suspensions can be used to control weeds and wild grasses in cotton crops.

Paste

The following substances are used to produce a 45% paste:
 45 parts of N-benzyl-2-[(2,6-dichloro-3-pyridyl)-oxy]-propionic acid amide,
 5 parts of sodium aluminium silicate,
 14 parts of cetyl polyglycol ether with 8 moles of ethylene oxide,
 1 part of cetyl polyglycol ether with 5 moles of ethylene oxide,
 2 parts of spindle oil,
 10 parts of polyglycol (Carbowax),
 23 parts of water.

The active substance is intimately mixed and ground with the additives in suitable devices. A paste is obtained from which it is possible to produce, by dilution with water, suspensions of the desired concentration.

Emulsion concentrate

The following constituents are mixed together to produce a 10% emulsion concentrate:

10 parts of N,N-dimethyl-2-[(2,6-dichloro-3-pyridyl)-oxy]-propionic acid amide,
 15 parts of oleyl polyglycol ether with 8 moles of ethylene oxide,
 75 parts of isophorone (3,5,5-trimethylcyclohex-2-en-1-one).

This concentrate can be diluted with water to give emulsions of a suitable concentration. Such emulsions are suitable for combatting weeds in cultivated crops, such as in crops of soya beans and potatoes.

We claim:

1. A composition for regulating plant growth and for antagonising the action of strong herbicides on crops, which composition contains as active substance an effective amount of a 3-pyridyl-oxy-alkanecarboxylic acid amide of formula I

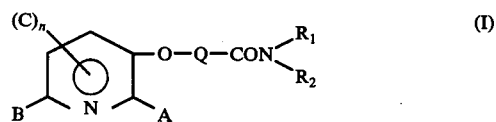

wherein
 A is a hydrogen or halogen atom, a $C_1$–$C_4$-alkyl group which can be substituted by halogen or hydroxy, the nitro or amino group, a $C_1$–$C_4$-alkoxy or $C_1$–$C_4$-alkylthio group,
 B has the same meaning as A,
 C is hydrogen, a halogen atom or the nitro group,
 n is 1 or 2,
 Q is an alkylene bridge member having 1–12 C atoms or an alkenylene bridge member having 2–12 C atoms which is branched or unbranched and which can be substituted by halogen, or phenyl,
 $R_1$ and $R_2$ independently of one another are each hydrogen, a $C_1$–$C_{12}$-alkyl group which is optionally substituted by OH or $C_1$–$C_4$-alkoxy, a $C_1$–$C_4$-alkoxy group, a $C_3$–$C_8$-alkenyl group, a $C_3$–$C_8$-alkynyl group, phenyl or benzyl, whereby the phenyl rings can also be substituted by halogen, $C_1$–$C_4$-alkoxy, $C_1$–$C_4$-alkylthio, $C_1$–$C_4$-alkyl, or $NO_2$, together with a suitable inert carrier therefor.

2. A 3-pyridyl-oxy-alkanecarboxylic acid amide according to formula I, claim 1, wherein A, B, C, n, $R_1$ and $R_2$ have the meanings given in claim 1, and
 Q is an alkylene bridge member or an alkenylene bridge member having 2 to 12 C atoms, which can be branched or unbranched and which can be substituted by halogen, or phenyl.

3. A 3-pyridyl-oxy-alkane-carboxylic acid amide according to formula I, claim 1, wherein
 A, B, C, n, $R_1$ and $R_2$ have the given meanings, and Q is a methylene bridge member, with the stipulation that if A is hydrogen, the amino or hydroxy-methyl group, B cannot be hydrogen, or is B is alkyl, A and C cannot simultaneously be hydrogen.

4. The 3-pyridyl-oxy-alkanecarboxylic acid amides according to formula I, claim 1, wherein A and B are each halogen, and C is hydrogen.

5. As a 3-pyridyl-oxy-alkanecarboxylic acid amide according to claim 1, N,N-Dimethyl-2-[(2,6-dichloropyridyl-3-)-oxy]-propionic acid amide.

6. As a 3-pyridyl-oxy-alkanecarboxylic acid amide according to claim 1, N,N-Dimethyl(2,6-dichloropyridyl-3-) oxy-acetic acid amide.

7. As a 3-pyridyl-oxy-alkanecarboxylic acid amide according to claim 1, N,N-Dimethyl-2-[(2-chloro-6-brompyridyl-3-)-oxy]-propionic acid amide.

8. As a 3-pyridyl-oxy-alkanecarboxylic acid amide according to claim 1, N,N-Dimethyl-2-(2-chloro-6-bromo-3-pyridyl)-oxy-acetic acid amide.

9. As a 3-pyridyl-oxy-alkanecarboxylic acid amide according to claim 1, N,N-Dimethyl-2-[(2,6-dibromo-3-pyridyl)-oxy]-propionic acid amde.

10. As a 3-pyridyl-oxy-alkanecarboxylic acid amide according to claim 1, N,N-Dimethyl-(2,6-dibromo-3-pyridyl)-oxy-acetic acid amide.

11. As a 3-pyridyl-oxy-alkanecarboxylic acid amide according to claim 1, N,N-Dimethyl-2-[(2,6-dimethyl-3-pyridyl)-oxy]-propionic acid amide.

12. As a 3-pyridyl-oxy-akanecarboxylic acid amide according to claim 1, N,N-Dimethyl-(2,6-dimethyl-3-pyridyl)-oxy-acetic acid amide.

13. As a 3-pyridyl-oxy-alkanecarboxylic acid amide according to claim 1, N,N-Dimethyl-2-[(2,6-dichloro-4-nitro-3-pyridyl)-oxy]-propionic acid amide.

14. As a 3-pyridyl-oxy-alkanecarboxylic acid amide according to claim 1, N,N-(2,6-dichloro-4-nitro-3-pyridyl)-oxy-acetic acid amide.

15. As a 3-pyridyl-oxy-akanecarboxylic acid amide according to claim 1, N,N-Dimethyl-2-[(2,6-dichloro-6-methyl-3-pyridyl)-oxy]-propionic acid amide.

16. As a 3-pyridyl-oxy-alkanecarboxylic acid amide according to claim 1, N,N-Dimethyl-(2,4-dichloro-6-methyl-3-pyridyl)-oxy-acetic acid amide.

17. As a 3-pyridyl-oxy-alkanecarboxylic acid amide according to claim 1, N,N-Dimethyl-[(2,4,6-tribromo-3-pyridyl)-oxy]-propionic acid amide.

18. As a 3-pyridyl-oxy-alkanecarboxylic acid amide according to claim 1, N,N-Dimethyl-(2,4,6-tribromo-3-pyridyl)-oxy-acetic acid amide.

19. A method for the regulation of dicotyledonous plant growth, which comprises applying to said plants an effective amount of a 3-pyridyl-oxy-alkanecarboxylic acid amide according to claim 1.

* * * * *